(12) United States Patent
Laub et al.

(10) Patent No.: US 6,932,904 B2
(45) Date of Patent: Aug. 23, 2005

(54) CHROMATOGRAPHIC DEVICE AND METHOD OF FORMING A CHROMATOGRAPHIC DEVICE

(75) Inventors: Charles F. Laub, San Jose, CA (US); Franco Spoldi, Morgan Hill, CA (US)

(73) Assignee: Alltech Associates Inc., Deerfield, IL (US)

( * ) Notice: Subject to any disclaimer, the term of this patent is extended or adjusted under 35 U.S.C. 154(b) by 0 days.

(21) Appl. No.: 10/114,528

(22) Filed: Apr. 2, 2002

(65) Prior Publication Data

US 2003/0183566 A1 Oct. 2, 2003

(51) Int. Cl.[7] .............................................. B01D 15/08
(52) U.S. Cl. ..................... 210/198.2; 210/232; 210/656
(58) Field of Search ............................. 210/198.2, 656, 210/659, 232, 450; 96/101, 106

(56) References Cited

U.S. PATENT DOCUMENTS

| | | | |
|---|---|---|---|
| 3,853,769 A | * 12/1974 | Miller, III ............... | 210/321.74 |
| 4,211,658 A | * 7/1980 | McDonald et al. ....... | 210/198.2 |
| 4,350,595 A | 9/1982 | Gunkel | |
| 4,361,482 A | 11/1982 | Teetz et al. | |
| 4,451,365 A | 5/1984 | Sattler et al. | |
| 4,597,866 A | 7/1986 | Couillard | |
| D285,290 S | 8/1986 | Shalon et al. | |
| 4,675,105 A | 6/1987 | Martin et al. | |
| 4,710,289 A | 12/1987 | Wermuth et al. | |
| 4,719,011 A | 1/1988 | Shalon et al. | |
| 4,737,292 A | 4/1988 | Ritacco et al. | |
| 4,769,141 A | 9/1988 | Couillard | |
| 4,806,238 A | * 2/1989 | Sattler et al. ............ | 210/198.2 |
| 4,861,473 A | * 8/1989 | Shackelford et al. ..... | 210/198.2 |
| 4,865,728 A | 9/1989 | Larsson | |
| 4,872,979 A | * 10/1989 | Golay ..................... | 210/198.2 |
| 4,876,005 A | * 10/1989 | America ................. | 210/198.2 |
| 4,882,047 A | 11/1989 | Shalon | |
| 4,888,112 A | * 12/1989 | Kronwald ................ | 210/198.2 |
| 4,891,133 A | 1/1990 | Colvin, Jr. | |
| 5,137,628 A | 8/1992 | Hart et al. | |
| 5,169,522 A | 12/1992 | Shalon et al. | |
| 5,188,730 A | * 2/1993 | Kronwald ................ | 210/198.2 |
| 5,192,433 A | 3/1993 | Shalon | |
| 5,213,683 A | 5/1993 | Mann | |
| 5,324,427 A | * 6/1994 | Traveset-Masanes et al. ....................... | 210/198.2 |
| 5,354,462 A | * 10/1994 | Perritt ...................... | 210/223 |
| 5,366,621 A | 11/1994 | Bidell | |
| 5,378,361 A | 1/1995 | Baeckstrum | |
| 5,423,982 A | 6/1995 | Jungbauer et al. | |

(Continued)

FOREIGN PATENT DOCUMENTS

| | | |
|---|---|---|
| EP | 0040663 A1 | 2/1981 |
| EP | 0040663 | 2/1981 |
| EP | 0040663 B1 | 9/1986 |

*Primary Examiner*—Ernest G. Therkorn
(74) *Attorney, Agent, or Firm*—William D. Bunch

(57) ABSTRACT

A chromatographic device comprises a tube, a chromatographic medium, a piston assembly, and a locking mechanism. The tube comprises first and second opposite ends and an inner surface. The inner surface of the tube at least in part defines an intermediate region. The intermediate region is generally between the first and second ends. The chromatographic medium is within the intermediate region. The piston assembly is within the tube and is positioned generally between the first end of the tube and the chromatographic medium. The piston assembly defines a passage for flow of process fluid. The piston assembly comprises a piston body portion. The locking mechanism is adjacent the piston assembly and is in engagement with the inner surface of the tube in a manner to prevent movement of the piston assembly relative to the tube axially toward the first end of the tube without preventing movement of the piston assembly relative to the tube axially toward the second end of the tube.

20 Claims, 4 Drawing Sheets

U.S. PATENT DOCUMENTS

| | | |
|---|---|---|
| 5,462,659 A | 10/1995 | Saxena et al. |
| 5,531,810 A | 7/1996 | Fullemann |
| 5,866,008 A | 2/1999 | Shalon et al. |
| 5,893,971 A | 4/1999 | Shalon et al. |
| 5,951,873 A | 9/1999 | Shalon et al. |
| 6,036,855 A | 3/2000 | Shalon et al. |
| 6,068,767 A * | 5/2000 | Garguilo et al. ......... 210/198.2 |
| 6,171,486 B1 | 1/2001 | Green et al. |

* cited by examiner

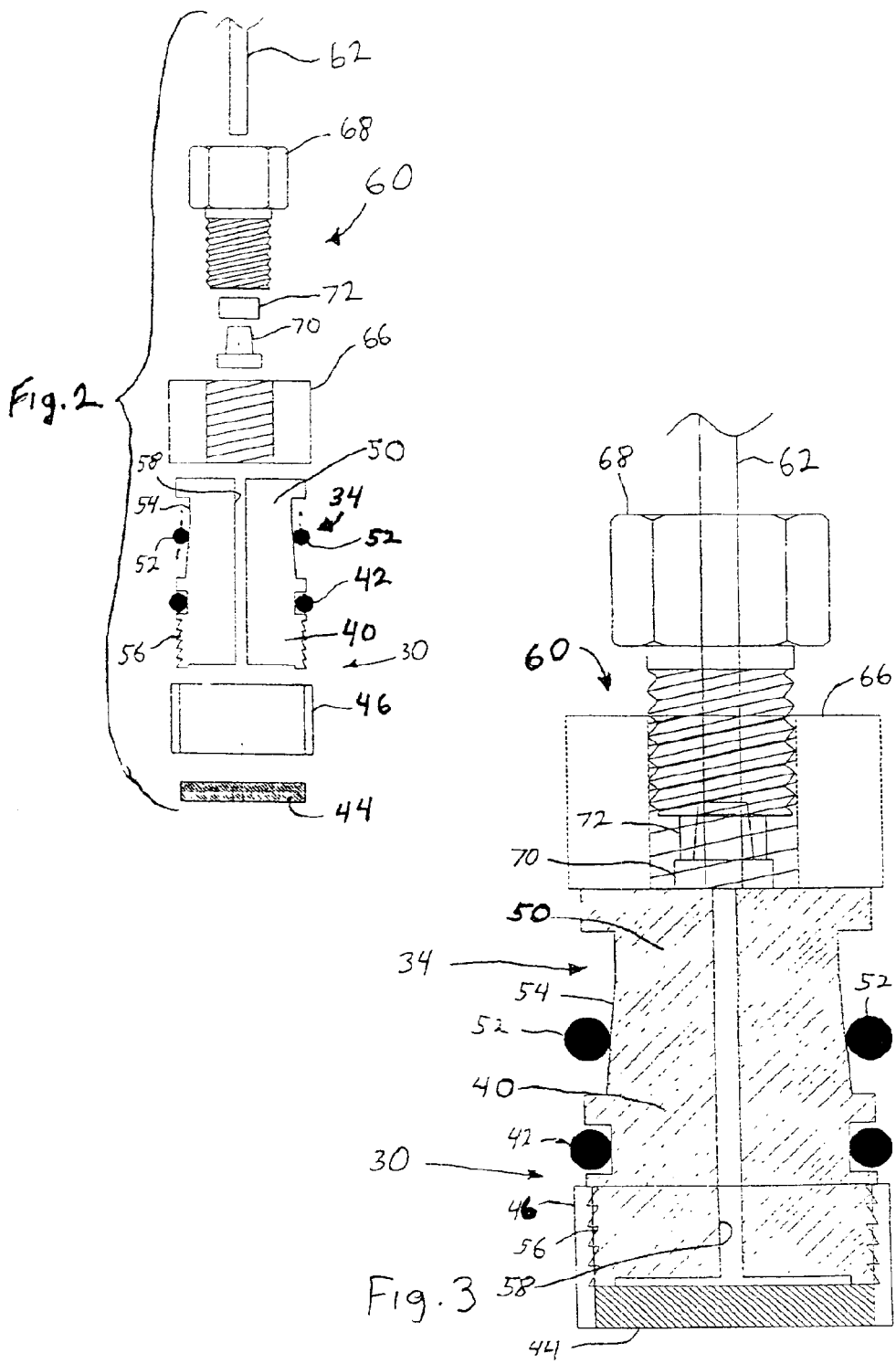

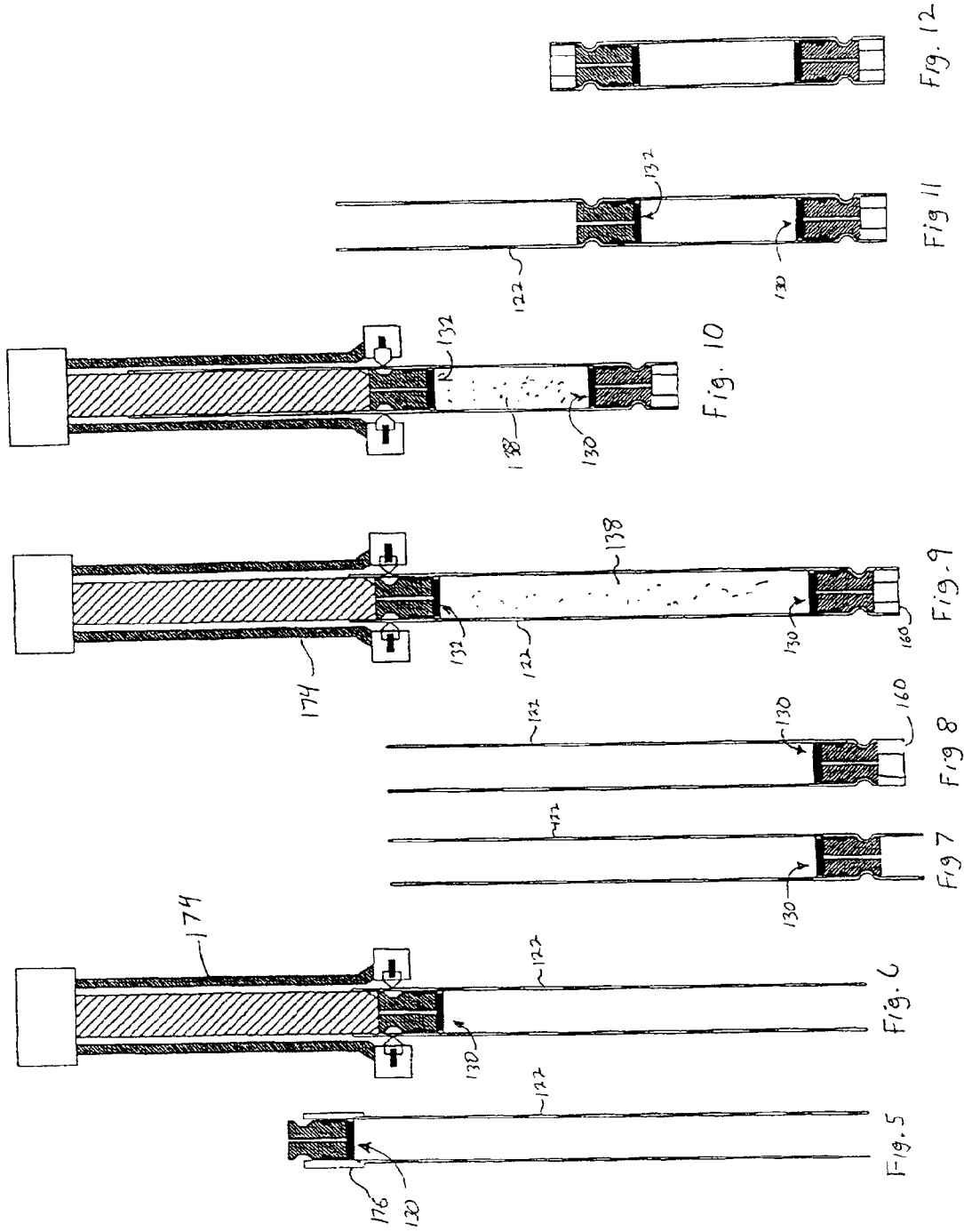

CHROMATOGRAPHIC DEVICE AND METHOD OF FORMING A CHROMATOGRAPHIC DEVICE

BACKGROUND OF THE INVENTION

This invention relates to the field of liquid chromatography, and more particularly to chromatographic devices having pistons for compressing a chromatographic medium.

Chromatography is a method of separating individual compounds in a mixture by distributing the compounds between heterogenous phases. A column packing material (or media), forming a stationary phase, generally has a large surface area through which a liquid mobile phase is allowed to flow. Chemical compounds in the mobile phase are maintained in the system for a time that is dependent upon the affinity of the particular compounds for the stationary phase. Multiple component mixtures can, with chromatography, be separated into single components in a single step procedure.

Chromatographic separations can be carried out efficiently in columns slurry packed with microparticulate media. The slurry is uniformly and rapidly compacted into a column under pressure. The slurry is maintained at high pressure and density to achieve efficient end results.

A chromatographic device generally includes a chromatographic column (having a cylindric column body and a fixed end plate covering one end of the column body), a piston slidable within the column body, an intake opening through the piston, a discharge opening through the end plate, a first porous frit seated within a frit-receiving socket of the piston and covering the intake opening, and a second porous frit secured to the end plate and covering the discharge opening. A slurry containing the packing material, such as a granular silica or polymeric media, is placed within the column body and the piston is moved toward the fixed end plate to compress the slurry. The pores of the frits are sized to permit the liquid of the slurry to flow out the discharge opening while preventing discharge of the packing material. Conventionally, when the chromatographic media within a chromatographic column is packed, a telescoping rod of a hydraulic pushing device pushes the piston into the column. This compression packs the packing material to a predetermined pressure (which may typically be around 1,000 to 5,000 p.s.i., but these values are merely exemplary rather than limiting).

With such conventional method of packing chromatographic columns, the column remains attached to the pushing device so that the rod of the hydraulic pushing device maintains the pushing force on the piston. In other words, the column must remain attached to the pushing device during operation of the chromatographic column, i.e., during chromatographic separations.

SUMMARY OF THE INVENTION

Among the several objects of the present invention may be noted the provision of an improved chromatographic device and method for forming a chromatographic device; the provision of such a device and method for forming a chromatographic device in which compression is maintained on a column piston even after removal of the column from a pushing device; the provision of such a device and method for forming a chromatographic device which is reliable and yet relatively inexpensive; and the provision of such a device in which a frit is sealed to a piston body in an improved manner.

Generally, a chromatographic device of one aspect of the present invention comprises a tube, a chromatographic medium, a piston assembly, and a locking mechanism. The tube extends longitudinally along a tube axis. The tube comprises first and second opposite ends and an inner surface. The inner surface of the tube at least in part defines an intermediate region. The intermediate region is generally between the first and second ends. The chromatographic medium is within the intermediate region. The piston assembly is within the tube and is positioned generally between the first end of the tube and the chromatographic medium. The piston assembly defines a passage for flow of process fluid. The piston assembly comprises a piston body portion. The locking mechanism is adjacent the piston assembly and is in engagement with the inner surface of the tube in a manner to prevent movement of the piston assembly relative to the tube axially toward the first end of the tube without preventing movement of the piston assembly relative to the tube axially toward the second end of the tube.

A chromatographic device of another aspect of the present invention comprises a tube, a chromatographic medium, a piston assembly, a frit, and a flexible sleeve. The tube extends longitudinally along a tube axis. The tube comprises first and second opposite ends and an inner surface. The inner surface of the tube at least in part defines an intermediate region. The intermediate region is generally between the first and second ends. The chromatographic medium is within the intermediate region. The piston assembly is within the tube and is positioned generally between the first end of the tube and the chromatographic medium. The piston assembly defines a passage for flow of process fluid. The piston assembly comprises a piston body portion. The frit is generally between the piston body portion and the chromatographic medium. The flexible sleeve engages both the piston body portion and the frit.

A chromatographic device of another aspect of the present invention comprises a tube, a chromatographic medium, and a piston assembly. The tube extends longitudinally along a tube axis. The tube comprises first and second opposite ends and an inner surface. The inner surface of the tube at least in part defines an intermediate region. The intermediate region is generally between the first and second ends. The chromatographic medium is within the intermediate region. The piston assembly is within the tube and is positioned generally between the first end of the tube and the chromatographic medium. The piston assembly defines a passage for flow of process fluid. The piston assembly comprises a piston body portion having an outer surface and a shoulder surface. The outer surface defines a peripheral boundary lying in a plane perpendicular to the tube axis. The shoulder surface is radially inward of the peripheral boundary. The tube is crimped such that the inner surface includes a piston engaging surface portion operatively engaging the shoulder surface of the piston body portion in a manner to prevent the piston assembly from moving axially toward the first end of the tube. The piston engaging surface portion is radially inward of the peripheral boundary.

A chromatographic device of another aspect of the present invention comprises a tube, a chromatographic medium, first and second piston assemblies, and first and second line connectors. The tube extends longitudinally along a tube axis. The tube comprises first and second opposite ends and an inner surface. The inner surface of the tube at least in part defines an intermediate region. The intermediate region is generally between the first and second ends. The chromatographic medium is within the intermediate region. The first piston assembly is within the tube and is positioned generally between the first end of the tube and the chromatographic medium. The first piston assembly defines a first passage for flow of process fluid, The first piston assembly comprises a first piston body portion. The second piston assembly is within the tube and is positioned generally between the second end of the tube and the chromatographic medium. The second piston assembly defines a second passage for flow of process fluid. The second piston assembly comprises a second piston body portion. The first line connector is within the tube and between the first piston body portion and the first end of the tube. The first line connector and the first piston body portion are separate members. The second line connector is within the tube and is between the second piston body portion and the second end of the tube. The second line connector and the second piston body portion are separate members. The first line connector is adapted for connection thereto of a fluid feed line and the second line connector is adapted for connection thereto of a fluid discharge line.

A method of the present invention for forming a chromatographic device comprises providing a tube having a primary end, a secondary end margin defining a secondary end opposite the primary end, and an inner surface, the tube extending longitudinally along a tube axis. The method further comprises providing a piston assembly. The method further comprises placing a chromatographic medium in the tube and inserting the piston assembly into the tube such that the piston assembly is between the chromatographic medium and the secondary end, moving the piston assembly along the tube axis and toward the primary end such that the piston assembly is between the secondary end margin and the chromatographic medium, and removing the secondary end margin of the tube from rest of the tube. The removing step occurs after the moving step.

Other objects and features will be in part apparent and in part pointed out hereinafter.

BRIEF DESCRIPTION OF THE DRAWINGS

FIG. 2 is an exploded side-elevational view of a piston assembly and locking mechanism of the chromatographic column of FIG. 1 with some of the components thereof being shown in section;

FIG. 3 is an assembled side-elevational view of the piston assembly and locking mechanism of FIG. 2;

FIGS. 5–12 are longitudinal section views of steps for making the chromatographic column of FIG. 4.

Corresponding reference characters indicate corresponding parts throughout the several views of the drawings.

DESCRIPTION OF THE PREFERRED EMBODIMENTS

Figure 1:
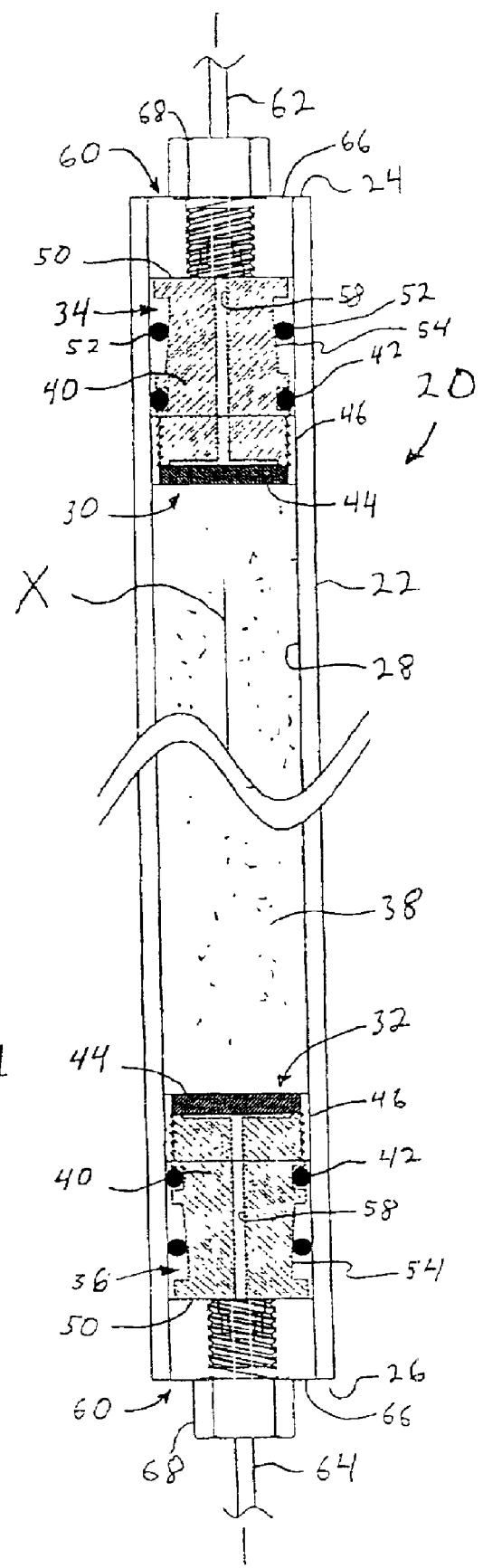
FIG. 1 is a longitudinal section view of a chromatographic column of the present invention with some of the components thereof being shown in section.

Referring now to the drawings and first more particularly to FIGS. 1–3, a chromatographic column of the present invention is indicated in its entirety by the reference numeral 20. The chromatographic column 20 comprises a chromatographic tube 22 extending longitudinally along a tube axis X. The tube comprises first and s second opposite ends 24, 26, both of which are preferably open, and an inner surface 28. The inner surface 28 of the tube 24 at least in part defines an intermediate region of the tube. The intermediate region is generally between the first and second ends 24, 26. The chromatographic column 20 preferably further comprises a first piston assembly, generally indicated at 30, a second piston assembly, generally indicated at 32, a first locking mechanism, generally indicated at 34, a second locking mechanism, generally indicated at 36, and a chromatographic medium 38.

Each of the first and second piston assemblies 30, 32 comprises a piston body portion 40, an o-ring seal 42, a frit 44, and a flexible sleeve 46 securing the frit to the piston body portion. Each of the first and second locking mechanisms 34, 36 comprises a locking body portion 50 and at least one bearing member 52. Preferably, the piston body portion 40 of the first piston assembly 30 and the locking body portion 50 of the first locking mechanism 34 are portions of a single monolithic part. Likewise, the piston body portion 40 of the second piston assembly 32 and the locking body portion 50 of the second locking mechanism 36 are preferably portions of a single monolithic part. Although each piston body portion and corresponding locking body portion are preferably of a single monolithic part, it is to be understood that the piston body portion and locking body portion may alternatively be separate parts (preferably secured together), without departing from the scope of this invention.

The first locking mechanism 34 is adapted to engage the inner surface of the tube 22 in a manner to prevent movement of the first piston assembly 30 relative to the tube axially (i.e., along the tube axis X) toward the first end 24 of the tube without preventing movement of the first piston assembly relative to the tube axially toward the second end 26 of the tube. The second locking mechanism 36 is adapted to engage the inner surface of the tube 22 in a manner to prevent movement of the second piston assembly 32 relative to the tube axially (i.e., along the tube axis X) toward the second end 26 of the tube without preventing movement of the second piston assembly relative to the tube axially toward the first end 24 of the tube.

Each of the first and second locking mechanisms 34, 36 has a tapered groove 54 (preferably in the form of a conic section as shown in FIGS. 1–3) in its locking body portion. The tapered groove 54 tapers radially inwardly such that the diameter of the portion of the tapered groove nearer the outer end of the locking body portion 50 is less than the diameter of the portion of the tapered groove nearer the piston body portion 40. Preferably, each locking mechanism 34, 36 comprises a plurality of bearing members 52, and the bearing members are preferably generally spherical in shape. The preferred number of bearing members 52 employed depends on the diameter of the tube 22. For example, five bearing members 52 are preferably employed with a tube 22 having an inside diameter of ten millimeters, seven to nine bearing members are preferably employed with a tube having an inside diameter of twenty millimeters, and fifteen to eighteen bearing members are preferably employed with a tube having an inside diameter of thirty millimeters. The bearing members 52 slide or roll in the tapered groove 54. Movement of the locking body portion 50 relative to the tube 22 along the axis X in one direction causes the bearing members 52 to slide or roll relative to the locking body portion 50 in the opposite direction. As the bearing members 52 slide or roll along the locking body portion 50 toward the piston body portion 40, the slope of the tapered groove 54 forces the bearing members against the inner surface 28 of the tube 22. In other words, the bearing members 52 are adapted to be radially squeezed between the tapered surface of the groove 54 of the locking body portion 50 and the inner surface 28 of the tube 22. This squeezing (or wedging) of the bearing members 52 against the inner surface 28 of the tube 22 locks the locking mechanism and corresponding piston assembly against movement in one direction. In particular, the bearing members 52 of the first locking mechanism 34 lock the first locking mechanism and the first piston assembly 30 against movement toward the first end 24 of the tube 22 while permitting movement of the first locking mechanism and the first piston assembly axially toward the second end 26 of the tube (i.e., inwardly toward the chromatographic medium). Likewise, the bearing members 52 of the second locking mechanism 36 lock the second locking mechanism and the second piston assembly 32 against movement toward the second end 26 of the tube 22 while permitting movement of the first locking mechanism and the first piston assembly axially toward the first end 24 of the tube (i.e., inwardly toward the chromatographic medium 38).

As discussed generally above, each of the piston assemblies 30, 32 comprises the piston body portion 40, o-ring seal 42, frit 44 and flexible sleeve 46. Preferably the o-ring seal 42 is of Viton® encapsulated in a polytetrafluoroethylene (PTFE or Teflon®) coating. The o-ring seal 42 circumscribes the piston body portion 40 and rests in a circumferential groove in the piston body portion. In operation, the frit 44 is generally between the end of the piston body portion 40 and the chromatographic medium 38. The flexible sleeve 46 preferably comprises a polymeric material (e.g., PTFE), and more preferably comprises a heat-shrinkable material (e.g., a heat-shrinkable PTFE). The flexible sleeve 46 circumscribes the periphery of the frit 44 and the end margin of the piston body portion 40 to secure the frit to the piston body portion and to seal against fluid leakage between the frit and the piston body portion. Preferably, the flexible sleeve 46 is heat shrunk on the frit 44 and end margin of the piston body portion 40 to form a snug fit of the sleeve around the frit and end margin of the piston body portion. Preferably, the end margin of the piston body portion 40 includes a plurality of relatively sharp circumferential ridges 56 shaped and adapted to grip the flexible sleeve 46 to prevent movement of the sleeve and frit 44 relative to the piston body portion.

Attachment of the frit 44 to the piston body portion 40 is shown in FIGS. 2 and 3. The frit 44 is placed against the open end of the piston body portion 40 and the flexible sleeve 46 is placed over the frit and the end margin of the piston body portion as shown in FIG. 2. The flexible sleeve 46 is then heated by a suitable heat source (such as a heat gun or by an oven) to cause the sleeve to shrink onto the frit 44 and the piston body portion 49 as shown in FIG. 3. The piston assembly is then pushed through an empty tube section (such as the chromatographic tube 22) to force the flexible sleeve onto the sharp ridges 56 on the end margin of the piston body portion 40. The piston assembly is then removed from the tube section and excess sleeve material is removed using a sharp knife or blade (not shown).

Referring now to FIGS. 2 and 3, each piston body portion/locking body portion combination includes a through bore 58 defining a passage for flow of process fluid. A line connector, generally indicated at 60, is attached to each locking body portion 50. The line connector 60 corresponding to the first locking mechanism 34 and first piston assembly 30 is adapted for connection thereto of a fluid feed line 62. The line connector 60 corresponding to the second locking mechanism 36 and second piston assembly 32 is adapted for connection thereto of a fluid discharge line 64. The line connector 60 comprises a fitting attachment block 66, a fitting nut 68, a tapered fitting ferule 70, and a lock ring 72. Preferably, each fitting attachment block 66 is secured to its corresponding locking body portion 40 by a suitable adhesive. The ferule 70 surrounds an end margin of its corresponding fluid line 62 or 64. The lock ring 72 surrounds the tapered ferule 70. The nut 68 has a central opening for passage of the fluid line. The nut 68 is attached to the attachment block 66 via mating threads. Threading the nut 68 into the attachment block 66 pushes the lock ring 72 toward the piston body 40. The lock ring 72 has a tapered inner surface which engages a tapered outer surface of the ferule 70. Because of these tapered surfaces, movement of the lock ring 72 toward the piston body 40 compresses the ferule 70 radially inwardly against the end of the fluid line 62 or 64 to provide a fluid tight seal between the fluid line and the through bore 58 of the piston body portion. In other words, the line connector 60 provides fluid communication between the fluid line 62 or 64 and the bore 58 through the piston body portion 40 while sealing against leakage there between. Preferably, the line connector 60 comprises a line connector of the type commercially available from Upchurch Scientific, Oak Harbor, Wash. The line connector 60 facilitates attachment of a variety of different size fluid lines to the piston body portion 40 without the need to modify the piston body portion. If one size fluid line (e.g., ⅛ inch diameter) is desired, one size fitting nut, fitting ferule and lock ring are employed. If another size fluid line (e.g., 1/16 inch diameter) is desired, another size fitting nut, fitting ferule and lock ring are employed. Thus, only the fitting nut, fitting ferule, and lock ring need to be replaced to switch the size of the fluid line. Also, because the attachment block 66 is attached to its corresponding locking body portion 40, the attachment block may be of a different (preferably less-expensive) material than that of the locking body portion.

In operation, a frit 44 is attached to the end of the piston body portion 40 of each of the first and second piston assemblies 30, 32 via the flexible sleeves 46, and an attachment block 66 is secured to the end of the locking body portion 50 of each of the first and second locking mechanisms 34, 36. The first piston assembly 30 and first locking mechanism 34 are inserted frit first into the first end 24 of the tube 22. A chromatographic medium 38 is poured or otherwise placed into the tube and the second piston assembly 32 and second locking mechanism 36 are inserted frit first into the second end 26 of the tube 22. Pressure is applied to the assemblies to move at least one the assemblies along the tube axis X toward the other of the assemblies to compress the chromatographic medium 38. Once the chromatographic medium has been compressed to the desired amount, the source of pressure is removed from the assemblies. The locking assemblies 34, 36 permit movement of the piston assemblies 30, 32 toward the chromatographic medium 38 but resist movement of the piston assemblies away from the chromatographic medium. The fluid feed line 62 and the fluid discharge line 64 are then aligned with the bores 58 and secured to the locking mechanisms 34, 36 via the fitting nuts 68, fitting ferules 70 and lock rings 72.

Figure 4:
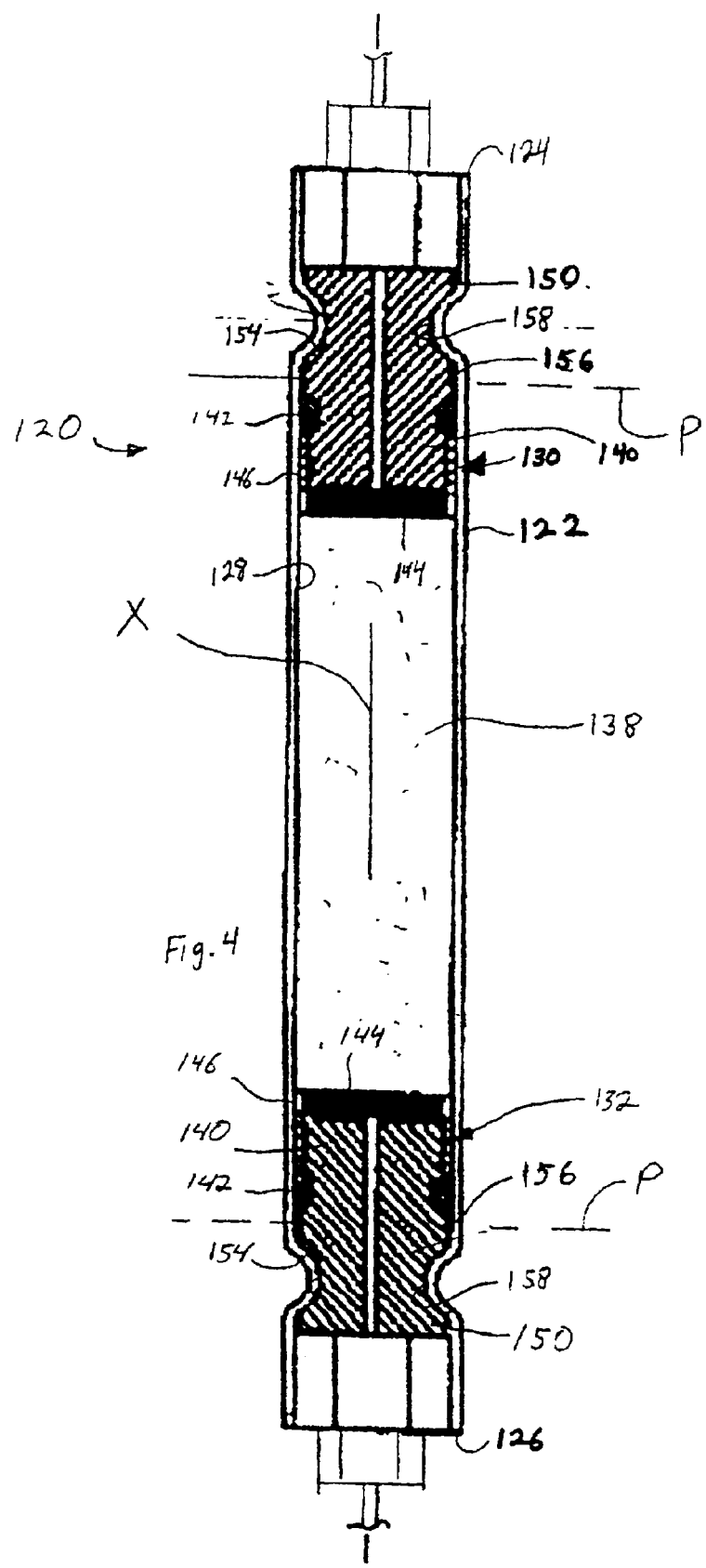
FIG. 4 is a longitudinal section view of a chromatographic column of a second embodiment of the present invention.

Referring now to FIG. 4, another preferred embodiment of a chromatographic column of the present invention is indicated in its entirety by the reference numeral 120. The chromatographic column 120 is similar to the chromatographic column 20 of FIGS. 1–3, except for the manner in which the piston assemblies are locked to the inner surface of the tube. As discussed in greater detail below, in the chromatographic column 120, the piston assemblies are locked to the inner surface of the tube by crimps in the tube.

The chromatographic column 120 comprises a chromatographic tube 122 extending longitudinally along a tube axis X. The tube 122 comprises first and second opposite ends 124, 126, both of which are preferably open, and an inner surface 128. The inner surface 128 of the tube 124 at least in part defines an intermediate region of the tube. The intermediate region is generally between the first and second ends 124, 126. The chromatographic column 120 preferably further comprises a first piston assembly, generally indicated at 130, a second piston assembly, generally indicated at 132, and a chromatographic medium 138.

Each of the first and second piston assemblies 130, 132 comprises a piston body portion 140, an o-ring seal 142, a frit 144, and a flexible sleeve 146 securing the frit to the piston body portion. Adjacent each piston body portion 140 is a locking body portion 150. Preferably, the piston body portion 140 and the locking body portion 150 are portions of a single monolithic part. The locking body portion 150 has an outer surface 152 and a shoulder surface 154 (preferably in the form of a circumferential groove). The outer surface 152 defines a peripheral boundary 156 lying in a plane P perpendicular to the tube axis X. The shoulder surface 154 is radially inward of the peripheral boundary 156. As shown in FIG. 4, the tube 122 is crimped such that the inner surface 128 of the tube includes a locking body engaging surface portion 158 engaging the shoulder surface 154 of the locking body portion in a manner to prevent the first piston assembly 130 from moving axially toward the first end 124 of the tube. The locking body engaging surface portion 158 is radially inward of the peripheral boundary 156. The chromatographic column 120 also preferably includes line connectors 160 the same as the line connectors 60 of the chromatographic column 20 of FIGS. 1–3.

The formation of the chromatographic column of FIG. 4 is shown in FIGS. 5–12. First, one of the piston assemblies (e.g., the first piston assembly 130) is placed in an end of the tube 122, as shown in FIG. 5, via a pressing/crimping apparatus 174 (shown in FIG. 6. Preferably a tapered insertion member 176 (FIG. 5) is temporarily attached to the end of the tube 122 to facilitate insertion of the piston assembly into the tube. Alternatively, the end of the tube could be flared in a separate flaring step (not shown). After the piston assembly 130 is positioned in the tube 122, the crimping mechanism 174 crimps the tube. The term "crimping" refers to mechanical reduction of the tube around another part to attach the two together. Preferably, the tube is crimped by a roll grooving crimping technique. In the "roll grooving" crimping technique a set of opposing wheels is driven against the tube wall perpendicular to the tube axis X using two or more small displacement hydraulic cylinders. The wheels are rotated around the outside of the tube 122 at the same time. This produces a uniform groove in the tube wall to form the locking body engaging surface portion 158.

As shown in FIG. 7, the tube 122 is removed from the pressing/crimping apparatus 174 and inverted. As shown in FIG. 8, excess tubing adjacent the first piston assembly 130 is removed and an attachment block of a line connector 160 is adhesively secured to the locking body portion 150 and the inner surface of the end margin of the tube 122. The chromatographic medium 138, preferably in the form of a slurry, is poured into the tube and the second piston assembly 132 is inserted into the second end of the tube 122 (see FIG. 9). Referring now to FIG. 10, the pressing/crimping apparatus 174 is then operated to push the second piston assembly 132 into the tube 122 toward the first piston assembly 130 to compress the chromatographic medium 138. The pressing/crimping apparatus 174 is then operated to crimp the tube 122 (FIG. 11) to form the locking body engaging surface portion 158 to secure the tube to the locking body portion 150 associated with the second piston assembly 132. As shown in FIG. 12, excess tubing adjacent the second piston assembly 132 is removed and an attachment block of a line connector 160 is adhesively secured to the locking body portion 150 and the inner surface of the end margin of the tube 122, thus resulting in the chromatographic column of FIG. 4.

In view of the above, it will be seen that the several objects of the invention are achieved and other advantageous results attained.

As various changes could be made in the above constructions and methods without parting from the scope of the invention, it is intended that all matter contained in the above description or shown in the accompanying drawings shall be interpreted as illustrative and not in a limiting sense.

What is claimed is:

1. A chromatographic device comprising:
    a tube extending longitudinally along a tube axis, the tube comprising first and second opposite ends, and an inner surface, the inner surface of the tube at least in part defining an intermediate region, the intermediate region being generally between the first and second ends;
    a chromatographic medium within the intermediate region;
    a piston assembly within the tube and positioned generally between the first end of the tube and the chromatographic medium, the piston assembly defining a passage for flow of process fluid, the piston assembly comprising a piston body portion; and
    a locking mechanism adjacent the piston assembly and engaging the inner surface of the tube in a manner to prevent movement of the piston assembly relative to the tube axially toward the first end of the tube without preventing movement of the piston assembly relative to the tube axially toward the second end of the tube.

2. A chromatographic device as set forth in claim 1 wherein the locking mechanism comprises a locking body portion and at least one bearing member, the bearing member being adapted to be radially squeezed between the locking body portion and the inner surface of the tube.

3. A chromatographic device as set forth in claim 2 wherein the locking body portion has a tapered outer surface, the bearing member being adapted to be radially squeezed between the tapered outer surface of the locking body portion and the inner surface of the tube.

4. A chromatographic device as set forth in claim 2 wherein the locking body portion of the locking mechanism and the piston body portion of the piston assembly constitute portions of a single unitary piece.

5. A chromatographic device as set forth in claim 2 wherein the bearing member is adapted to slide axially along the locking body portion.

6. A chromatographic device as set forth in claim 1 wherein the piston assembly comprises a first piston assembly and the locking mechanism comprises a first locking mechanism, the chromatographic device further comprising:
    a second piston assembly within the tube and positioned generally between the second end of the tube and the chromatographic medium, the second piston assembly defining a second passage for flow of process fluid; and
    a second locking mechanism adjacent the second piston assembly and engaging the inner surface of the tube in a manner to prevent movement of the second piston assembly relative to the tube axially toward the second end of the tube without preventing movement of the second piston assembly relative to the tube axially toward the first end of the tube.

7. A chromatographic device as set forth in claim 1 wherein the piston assembly further comprises a frit and a flexible sleeve, the flexible sleeve engaging both the piston body portion and the frit, the frit being generally between the piston body portion and the chromatographic medium.

8. A chromatographic device as set forth in claim 7 wherein the flexible sleeve comprises a polymeric material.

9. A chromatographic device as set forth in claim 1 further comprising a line connector within the tube and between the piston body portion and the first end of the tube, the line connector being adhered to the inner surface of the tube, the line connector being adapted for connection thereto of a fluid supply line for passage of process fluid, the line connector and the piston body portion being separate members.

10. A chromatographic device as set forth in claim 9 wherein the line connector is of a material different than that of the piston body portion.

11. A chromatographic device comprising:
   a tube extending longitudinally along a tube axis, the tube comprising first and second opposite ends, and an inner surface, the inner surface of the tube at least in part defining an intermediate region, the intermediate region being generally between the first and second ends;
   a chromatographic medium within the intermediate region;
   a piston assembly within the tube and positioned generally between the first end of the tube and the chromatographic medium, the piston assembly defining a passage for flow of process fluid, the piston assembly comprising a piston body portion;
   a frit generally between the piston body portion and the chromatographic medium;
   a flexible sleeve engaging both the piston body portion and the frit; and
   a locking mechanism adjacent the piston assembly and engaging the inner surface of the tube in a manner to prevent movement of the piston assembly relative to the tube axially toward the first end of the tube without preventing movement of the piston assembly relative to the tube axially toward the second end of the tube.

12. A chromatographic device as set forth in claim 11 wherein the flexible sleeve comprises a polymeric material and circumscribes the frit and an end margin of the piston body portion.

13. A chromatographic device as set forth in claim 12 wherein the flexible sleeve is of a heat-shrinkable material.

14. A chromatographic device as set forth in claim 13 wherein the flexible sleeve is heat shrunk on the frit and end margin of the piston body portion to form a snug fit of the sleeve around the frit and end margin of the piston body portion.

15. A chromatographic device as set forth in claim 11 wherein the polymeric material comprises polytetrafluoroethylene.

16. A chromatographic device comprising:
   a tube extending longitudinally along a tube axis, the tube comprising first and second opposite ends, and an inner surface, the inner surface of the tube at least in part defining an intermediate region, the intermediate region being generally between the first and second ends;
   a chromatographic medium within the intermediate region;
   a first piston assembly within the tube and positioned generally between the first end of the tube and the chromatographic medium, the first piston assembly defining a first passage for flow of process fluid, the first piston assembly comprising a first piston body portion;
   a second piston assembly within the tube and positioned generally between the second end of the tube and the chromatographic medium, the second piston assembly defining a second passage for flow of process fluid, the second piston assembly comprising a second piston body portion;
   a first locking mechanism adjacent the first piston assembly and engaging the inner surface of the tube in a manner to prevent movement of the first piston assembly relative to the tube axially toward the first end of the tube without preventing movement of the first piston assembly relative to the tube axially toward the second end of the tube.

17. A chromatographic device as set forth in claim 16 further comprising:
   a second locking mechanism adjacent the second piston assembly and engaging the inner surface of the tube in a manner to prevent movement of the second piston assembly relative to the tube axially toward the second end of the tube without preventing movement of the second piston assembly relative to the tube axially toward the first end of the tube.

18. A chromatographic device as set forth in claim 16, further comprising:
   a first line connector within the tube and between the first piston body portion and the first end of the tube, the first line connector and the first piston body portion being separate members; and
   a second line connector within the tube and between the second piston body portion and the second end of the tube, the second line connector and the second piston body portion being separate members;
   the first line connector being adapted for connection thereto of a fluid feed line and the second line connector being adapted for connection thereto of a fluid discharge line.

19. A chromatographic device as set forth in claim 18 wherein the first and second line connectors are adhered to the inner surface of the tube.

20. A chromatographic device as set forth in claim 18 wherein the first line connector is of a material different than that of the first piston body portion and the second line connector is of a material different that that of the second piston body portion.

* * * * *